United States Patent [19]

Auge et al.

[11] 3,931,252
[45] Jan. 6, 1976

[54] PROCESS FOR THE PREPARATION OF PURE 1-NITROANTHRAQUINONE

[75] Inventors: Wolfgang Auge, Odenthal; Bernd Thelen, Leverkusen; Karl-Werner Thiem, Cologne; Rutger Neeff, Leverkusen, all of Germany

[73] Assignee: Bayer Aktiengesellschaft, Leverkusen-Bayerwerk, Germany

[22] Filed: Nov. 16, 1973

[21] Appl. No.: 416,642

[30] Foreign Application Priority Data
Nov. 18, 1972 Germany............................ 2256644

[52] U.S. Cl. ................................................ 260/369
[51] Int. Cl.$^2$......................................... C07C 79/37
[58] Field of Search ..................................... 260/369

[56] References Cited
UNITED STATES PATENTS

| | | | |
|---|---|---|---|
| 2,874,168 | 2/1959 | Graham et al...................... | 260/369 |
| 3,766,222 | 10/1973 | Hartwig et al. ..................... | 260/369 |
| 3,798,243 | 3/1974 | Toth .................................. | 260/369 |
| 3,798,244 | 3/1974 | Mueller et al. ..................... | 260/369 |

FOREIGN PATENTS OR APPLICATIONS

| | | | |
|---|---|---|---|
| 281,490 | 1/1914 | Germany ........................... | 260/369 |
| 2,227,340 | 12/1972 | Germany ........................... | 260/369 |
| 2,103,360 | 8/1971 | Germany ........................... | 260/369 |
| 2,220,377 | 11/1972 | Germany ........................... | 260/369 |

*Primary Examiner*—Lorraine Weinberger
*Assistant Examiner*—E. Jane Skelly
*Attorney, Agent, or Firm*—Plumley & Tyner

[57] ABSTRACT

Process for the manufacture of pure 1-nitroanthraquinone, characterised in that a nitroanthraquinone mixture obtained by nitration of anthraquinone in the presence of inorganic acids and, optionally, lowering the molar fraction of the acids in the reaction mixture after isolation of the reaction products which have precipitated and, optionally, further measures, is subjected to a rectification.

10 Claims, No Drawings

PROCESS FOR THE PREPARATION OF PURE 1-NITROANTHRAQUINONE

The previously known processes for the preparation of 1-nitroanthraquinone by nitration of anthraquinone give product mixtures which must be subjected to purification operations in order to obtain a pure 1-nitroanthraquinone.

Thus, for example, a process for the nitration of anthraquinone in sulphuric acid by means of nitric acid is known from German Offenlegungsschrift (German Published Specification) 2,039,822. Even using the best embodiment of this process, the crude product must be purified by washing with acid amides, for example dimethylformamide. 95–96% pure 1-nitroanthraquinone is obtained in 42% yield. A disadvantage of this process is that organic solvents are used, the recovery of which, in special apparatuses, is difficult and expensive, solvent losses being unavoidable.

Further, German Offenlegungsschrift (German Published Specification) 2,103,360 has disclosed a process for the manufacture of 1-nitroanthraquinone in phosphoric acid and nitric acid in which a part of the impurities remains in the phosphoric acid. In this process, a 1-nitroanthraquinone of which the purity, in the best embodiment, reaches about 96%, is obtained in 43% yield.

A variant of this process is described in German Offenlegungsschrift (German Published Specification) 2,142,100 in which the nitration product is purified by treatment with halogenated hydrocarbons, for example dichloroethane. The yield of 1-nitroanthraquinone can thus be increased to 49% (of theory); however, the purity does not exceed 92%. Further, using organic solvents throws up the technological problems already mentioned.

German Offenlegungsschrift (German Published Specification) 2,162,538 describes the nitration of anthraquinone in nitric acid, of concentrations exceeding 90%, the molar ratio of anthraquinone to nitric acid being at least 1:20. A part of the by-products can be removed by diluting the acid with water, so that 1-nitroanthraquinone is obtained in 74.5% yield, but its purity does not exceed 92%.

Similar results are obtained if the nitration of anthraquinone with nitric acid is carried out in other media, for example in organic solvents or in hydrofluoric acid.

1-Nitroanthraquinone is an important intermediate product for the manufacture of 1-aminoanthraquinone, which in turn is the starting product for the manufacture of numerous dyestuffs. Since the by-products which are formed in the nitration of anthraquinone interfere with the multi-stage conversion of 1-nitroanthraquinone to dyestuffs, the quality of the dyestuffs is considerably impaired by the secondary products of the impurities, as already established in German Offenlegungsschrift (German Published Specification) 2,162,538.

There has therefore been no lack of attempts to produce 1-nitroanthraquinone, suitable for the preparation of anthraquinone dyestuffs, by further purification operations. Thus, for example, attempts have been made to purify crude 1-nitroanthraquinone by repeated crystallisation (Zeitschrift für Elektrochemie 7, 797 (1901)). Further, Chem. and Ind., 41, 1070 (1953) states that a crude separation of the products is achieved by dissolving in concentrated sulphuric acid and fractionally precipitating the nitration products by gradual dilution of the acid with water. Also, processes are known from U.S. Pat. No. 2,302,729 and German Offenlegungsschrift (German Published Specification) 2,206,960, in which the crude or pre-purified nitration products of anthraquinone can be purified further by boiling with aqueous alkali metal sulphite solution. The degree of purity of the 1-nitroanthraquinone achievable by this process is between 87 and 97%. The impurities are essentially anthraquinone and dinitroanthraquinone.

However, the sulphite purification process suffers from serious disadvantages since a part of the nitration products, including a part of the 1-nitroanthraquinone, is converted into water-soluble products of undefined composition and therefore leads to substantial contamination of effluents. Since it has hitherto not been possible to develop a process for recovering an industrially utilisable product from the filtrates of the sulphite purification process, this process entails a loss of anthraquinone derivatives.

German Pat. No. 281,490 states that crude 1-nitroanthraquinone can be converted easily into pure 1-nitroanthraquinone by distillation in vacuo. On repeating this process, however, it was only possible to obtain 86% pure 1-nitroanthraquinone in 74% yield. Whilst the purity can be improved by variations in the preparation of the crude product and in the distillation, it does not exceed 90–92%, and the yield is reduced considerably.

All these purification operations however fail to give 1-nitroanthraquinone which is sufficiently pure for further dyestuff syntheses. Thus, for example, German Offenlegungsschrift (German Published Specification) 2,206,960 shows that in the manufacture of 1-amino-4-bromo-anthraquinone-2-sulphonic acid by reduction of 1-nitroanthraquinone with sodium sulphide, subsequent sulphonation and bromination, an additional filtration process is necessary to remove the anthraquinone still present in the 1-nitroanthraquinone used as the starting material.

It is all the more surprising that 1-nitroanthraquinone which is sufficiently pure for the manufacture of dyestuffs (99–99.7% pure) is obtained if a nitroanthraquinone mixture obtained by nitration of anthraquinone in the presence of inorganic acids and optionally by lowering the molar fraction of the acids in the reaction mixture, after isolation of the reaction products which have precipitated and, optionally, further measures, is subjected to a rectification.

It is possible to use nitroanthraquinone mixtures which are obtained, for example, by the abovementioned processes, such as nitration of anthraquinone in nitric acid or sulphuric acid, with subsequent partial removal of the impurities by dilution of the acids with water, by nitration of anthraquinone in phosphoric acid and other solvents or by the sulphite treatment of nitration mixtures manufactured in any desired way.

A preferred embodiment of the process according to the invention for the preparation of particularly pure 1-nitroanthraquinone is characterised in that anthraquinone is nitrated in highly concentrated nitric acid, especially in the concentration range of over 90%, at temperatures in the range of -40° to 80°C, especially of 20° to 60°C, using a molar ratio of nitric acid to anthraquinone of at least 4:1, especially of 8:1 to 19:1, and that subsequently the molar ratios of nitric acid to nitration products and the acid concentrations are adjusted to the following values by distilling off nitric acid and/or by dilution with water: from a molar ratio of 4:1, with a simultaneous acid concentration of 96%, to a molar ratio of 19:1 and an acid concentration of 75%. Preferred ranges are molar ratios of 6:1 with an acid concentration of 93% to molar ratios of 15:1 with an acid concentration of 79%. In this procedure, a part of the impurities also precipitates alongside 1-nitroanthraquinone.

The solubility of the products contained in the reaction mixture rises with the temperature and with the amount and concentration of nitric acid. Hence, to precipitate a certain proportion of the reaction product, the acid concentration must be adjusted to a relatively low value if the molar ratio of nitric acid to the reaction product is relatively high (and vice versa). Hence, with the limits indicated above, low acid concentrations correspond to high molar ratios and vice versa.

The 1-nitroanthraquinone which precipitates in this procedure is filtered off, dried and subjected to a vacuum distillation, especially a rectification. The temperatures and pressures quoted below indicate the conditions at the head of the distillation apparatus.

The distillation can be carried out at between 200° and 400°C under 0.5–100 mm Hg, especially at 235° to 330°C and 1.5–50 mm Hg, and preferably at 245° to 315°C and 2.5 to 35 mm Hg. It proves to be particularly advantageous to carry out the distillation at temperatures between 265° and 300°C, using a vacuum of 5 to 20 mm Hg. The entire process can be carried out discontinuously or continuously.

A special variant is that the pre-purified product is distilled together with a solvent which boils at 100° to 300°C, is stable under distillation conditions and is inert towards the product, for example high-boiling hydrocarbons or silicone oils, under the conditions indicated above, and the 1-nitroanthraquinone which has crystallised out is isolated from the condensate according to known processes.

The advantages of the process according to the invention reside firstly in the high purity (>99%) coupled with good yield (over 70%) and secondly in the fact that the purification process neither uses organic solvents nor produces chemically undefined waste products which are water-soluble and therefore contaminate effluents. Further advantages of this process are that dinitroanthraquinones, which are also valuable starting products for dyestuffs, can be isolated from the distillation residue and that the nitric acid produced can, after distillation and subsequent concentration, be re-used.

WORKING-UP OF A NITRATION MIXTURE OF ANTHRAQUINONE, ACCORDING TO GERMAN PAT. NO. 281,490.

A mixture of 208 g of anthraquinone and 763 g of 99% strength nitric acid (molar ratio 1:12) is stirred for 18 minutes at 45°C. The reaction product is then added to ice and the nitration product which precipitates is filtered off, washed until neutral and dried. The product is subjected to a fractional vacuum distillation at 295°C and 20 mm Hg and the distillate obtained is 218 g of 86% pure 1-nitroanthraquinone (74% of theory).

EXAMPLE 1

A mixture of 208 g of anthraquinone and 2,550 g of 99% strength nitric acid (molar ratio 1:40) is stirred for 10 minutes at 20°C and then diluted with 302 ml of water to an acid content of approx. 88% by weight. 1,350 g of 98% strength nitric acid are then distilled off in vacuo, resulting, in the sump, in a molar ratio of approx. 18:1 and an acid content of 78%. The precipitate which has separated out is filtered off, washed until neutral and dried. The product is subjected to a fractional vacuum distillation at 10 mm Hg, and a head temperature of 281°C. 181 g of 99.2% pure 1-nitroanthraquinone (71% of theory) are obtained as the distillate.

EXAMPLE 2

The nitration mixture obtained according to Example 1 is heated, in 250 ml of water, with 175 g of anhydrous sodium sulphite and 32.5 g of a 30% strength sodium hydroxide solution for 1 hour at 90°–95°C. The product is then filtered off hot, and the residue is washed with hot water until neutral and dried. The product is fractionally distilled at 15 mm Hg, and a head temperature of 292°C, and gives 170 g of 99.7% pure 1-nitroanthraquinone. (67% of theory).

EXAMPLE 3

A mixture of 208 g of anthraquinone and 1,210 g of 99% strength nitric acid (molar ratio 1:19) is stirred for 14 minutes at 35°C and subsequently adjusted to an acid content of 78% with 319 ml of water. The product which precipitates is filtered off, washed until neutral and dried. The product is subjected to a fractional distillation at 5 mm Hg, and a head temperature of 262°C. 99.4% pure 1-nitroanthraquinone is obtained as the distillate, in 69% yield (176 g).

EXAMPLE 4

A mixture of 208 g of anthraquinone and 763 g of 99% strength nitric acid (molar ratio 1:12) is stirred at 45°C for 18 minutes and then diluted to an acid content of approx. 90% with 51 ml of water. 193 G of 98% strength nitric acid are then distilled off in vacuo, resulting in an acid content of approx. 87%, and a molar ratio of approx. 8:1, in the sump. The product which precipitates is filtered off, washed until neutral and dried. Fractional distillation of the product at 6 mm Hg and a head temperature of 267°C gives 165 g of a 99.4% pure 1-nitroanthraquinone (65% of theory).

EXAMPLE 5

A pre-purified crude 1-nitroanthraquinone obtained according to Example 4 is distilled with 800 g of paraffin oil at 30 mm Hg and using head temperatures between 250° and 300°C. The 1-nitroanthraquinone which precipitates in the condensate is filtered off and freed from paraffin oil by washing with petroleum ether. 163 G of 99.4% pure 1-nitroanthraquinone (64% of the theory) are obtained.

EXAMPLE 6

A product obtained according to Example 4 is distilled with 800 g of silicone oil at 30 mm Hg, using head temperatures between 250° and 300°C. The product which precipitates is worked up according to the instructions of Example 5. The yield of 99.4% pure 1-nitroanthraquinone is 168 g (66% of theory).

We claim:

1. In the process for manufacturing pure 1-nitroanthraquinone wherein anthraquinone is nitrated with at least 90% by weight nitric acid or 90% by weight of a mixture of nitric acid and another inorganic acid at temperatures of −40° to +80°C; the improvement which comprises adjusting the acid content to from 76% at a molar ratio of acid to nitration products of 19:1 to 96% at a molar ratio of 4:1 after nitration has occurred, allowing crude 1-nitroanthraquinone to crystallize, and subsequently rectifying the precipitated reaction product at temperatures of 200° to 400°C and pressures of from 0.5 to 100 mm. of mercury.

2. The process of claim 1 wherein said nitration takes place with a molar ratio of acid to anthraquinone of from 4:1 to 19:1.

3. Process according to claim 1, characterised in that the nitroanthraquinone mixture obtained from the nitration is subjected to a treatment with alkali metal sulphites in the presence of water prior to the rectification.

4. Process according to claim 1, characterised in that the nitration of anthraquinone is carried out at temperatures of 20° to 60°C and molar ratios of nitric acid to anthraquinone of 8:1 to 19:1, the conditions are then adjusted to conditions between nitric acid concentrations of 79% at molar ratios of nitric acid to nitration products of 15:1 and nitric acid concentrations of 93% at molar ratios of 6:1, and the reaction product which precipitates is subjected to a rectification.

5. Process according to claim 1 characterized in that the reaction product is rectified together with a diluent with is inert under the rectification conditions and which boils between 100° and 300°C and the 1-nitroanthraquinone which crystallizes is isolated from the condensate.

6. Process of claim 5 wherein the diluent is selected from the group consisting of high-boiling hydrocarbons and silicone oils.

7. Process according to claim 5, characterised in that a hydrocarbon is used as diluent.

8. Process according to claim 7, characterised in that a paraffin is employed.

9. Process according to claim 5, characterised in that a silicone oil is employed as a diluent.

10. Process of claim 1 wherein the nitration is continuous.

* * * * *